(12) United States Patent
Lancesseur et al.

(10) Patent No.: US 7,475,773 B2
(45) Date of Patent: Jan. 13, 2009

(54) CONTAINER FOR MOISTURE-SENSITIVE GOODS

(75) Inventors: Didier Lancesseur, Boulogne Billancourt (FR); Sébastien Brogly, Saint-Just (FR)

(73) Assignee: Airsec S.A.S., Choisy le Roi (FR)

( * ) Notice: Subject to any disclaimer, the term of this patent is extended or adjusted under 35 U.S.C. 154(b) by 380 days.

(21) Appl. No.: 11/048,268

(22) Filed: Feb. 1, 2005

(65) Prior Publication Data

US 2006/0169603 A1 Aug. 3, 2006

(51) Int. Cl.
*B65D 81/26* (2006.01)
*B65D 39/00* (2006.01)
*B65D 43/14* (2006.01)
*B65D 51/04* (2006.01)
*F17C 11/00* (2006.01)

(52) U.S. Cl. .................. 206/204; 220/789; 220/839

(58) Field of Classification Search ................ 206/204; 220/789, 791, 801, 836, 837, 521–523, 213, 220/87.1, 839; 222/457.5
See application file for complete search history.

(56) References Cited

U.S. PATENT DOCUMENTS

| | | | | |
|---|---|---|---|---|
| 1,698,320 A | * | 1/1929 | Sharp | .................. 96/118 |
| 3,081,137 A | | 3/1963 | Lolokythas | |
| 3,254,784 A | | 6/1966 | Lancesseur | |
| 3,918,578 A | | 11/1975 | Cullen et al. | |
| 4,146,277 A | | 3/1979 | Santoro | |
| 4,805,789 A | | 2/1989 | Lancesseur | |
| 4,834,234 A | | 5/1989 | Sacherer et al. | |
| 5,432,214 A | | 7/1995 | Lancesseur | |
| 5,788,064 A | * | 8/1998 | Sacherer et al. | ............. 206/204 |
| 5,934,494 A | * | 8/1999 | Takahashi et al. | ........... 215/347 |
| 5,947,274 A | | 9/1999 | Taskis et al. | |
| 6,247,604 B1 | | 6/2001 | Taskis et al. | |
| 6,274,209 B1 | * | 8/2001 | Pagidas et al. | ............. 428/35.7 |
| 6,688,081 B2 | | 2/2004 | Boyd | |
| 6,688,501 B2 | * | 2/2004 | DeGroot et al. | ............. 222/556 |
| 6,971,531 B1 | * | 12/2005 | Dubach | ..................... 215/235 |
| 7,204,381 B2 | * | 4/2007 | Vincent et al. | ................ 215/44 |

FOREIGN PATENT DOCUMENTS

| | | |
|---|---|---|
| DE | 3622773 A1 | 1/1986 |
| DE | 19633595 A1 | 2/1996 |
| FR | 2623477 | 5/1989 |
| GB | 694625 | 7/1953 |
| GB | 731417 | 6/1955 |
| WO | WO 96/04189 | 2/1996 |

\* cited by examiner

*Primary Examiner*—Mickey Yu
*Assistant Examiner*—Melissa L Lalli
(74) *Attorney, Agent, or Firm*—John C. Thompson

(57) ABSTRACT

A container for moisture-sensitive goods, with a container bottom and a container wall and a cover which may be opened and closed, where the container cover is provided with a desiccant-containing body, the cover (16) having a cover base (36) and a cover lid (34) which are pivotable against each other, the cover base (36) having a through-opening (44). The cover lid carries sealing means for sealing the through-opening (44). A desiccant-containing body (70) is arranged at least partially surrounding the through-opening.

12 Claims, 2 Drawing Sheets

CONTAINER FOR MOISTURE-SENSITIVE GOODS

TECHNICAL FIELD

The present invention relates to a container for moisture-sensitive goods, and more particularly to a container for moisture-sensitive diagnostic test strips

BACKGROUND OF THE INVENTION

Containers for moisture-sensitive goods are widely known. As an example, a container for moisture-sensitive goods is known from WO 96/04189. This container is formed as a glass vial with a closure generally made of rubber material, with desiccant polymer being received in the lower portion of the closure. However, this container is not suitable for receiving moisture-sensitive goods such as test strips. It is required that single test strips may be taken out of the container, after opening the cover and closing it, while the remainder of the test strips must be kept dry over an extended period of time However, the container known from WO 96/04189 is not suitable for such goods which may be taken out deliberately.

On the other hand, it is known to provide a closure cap or cover of a container for moisture-sensitive goods such as drugs with a desiccant-containing body. Such containers are widely used. Early examples are shown in U.S. Pat. No. 4,145,277 and U.S. Pat. No. 3,918,578. The desiccant-containing material is received in a compartment formed on the lower portion of the cover or cap with a cardboard disk separating the desiccant from the drugs etc.

However, the cardboard or other disk used for this purpose must be selected carefully in order to avoid any pollution of the goods by the cardboard material. In any case, small fibers may separate from the cardboard disk and spoil the moisture-sensitive goods which is not acceptable in some cases.

Thus, it has been proposed to provide containers with desiccant containing bodies formed as solid bodies and protruding from the cap or cover. However, such bodies must be quite big as the moisture from the environment significantly attacks the desiccant-containing body if the cap is taken off. Moreover, the desiccant-containing body may be subject to damage if it is laid down on a table or the like.

OBJECTS AND SUMMARY OF THE INVENTION

The object underlining this invention is to provide a container for moisture-sensitive goods such as tests strips or other goods which may be taken out deliberately and on a piece-by-piece basis, the goods having an increased life time.

The inventive solution provides a cover made from two parts, namely a cover base and a cover lid. A desiccant-containing body is received at the lower surface of the cover base which in use stays on top of the container.

Only the cover lid is opened for taking out the goods such that only a limited portion of environmental moisture may contact the desiccant-containing body. This advantage greatly increases the life time of the desiccant-containing body such that the goods received in the container are kept dry over an extended time, even if a small desiccant body is used.

According to an advantageous development, the desiccant-containing body has an essentially truncated triangular profile. By this, only small areas of the body are close to the through-opening. A significant advantage arises when using goods such as test strips. With this form of the body, the lower walls of the body convert toward through-opening, viewing from the underside of the body, such that the goods are automatically supplied toward the through-opening when turning the container upside down.

This effect also applies to goods other than strips, but with strips, it has been particularly difficult to take out a single strip without taking off the cover base.

With the inventive solution, a central through-opening is provided in the cover base which is firmly sealed by sealing means provided between the cover lid and the cover base. As an example, a suitable projection may be formed on the lower portion of the cover lid such that this projection may enter the through-openings to form the sealing means.

The cover base has essentially a L-shape, with the desiccant-containing body being received between the legs of L, or within the cover base. By this, no further fixing means are required such that any pollution by adhesive or the like may be avoided.

The desiccant-containing body formed according to the invention may be manufactured by pressing it in the corresponding part of the cover base. Alternatively, the cover base may be formed with the desiccant-containing body as a base.

A second alternative is a press-fit between the cover base and the desiccant-containing body.

It is preferred that the desiccant-containing body is fully received in the cover base, i.e. it does not protrude from the lower leg thereof. However, any other suitable form may be selected as well and the oblique or conical inner or lower surface may be shaped flat, convex or concave, dependent on the goods to be received in the inventive container.

The container base may have a flat upper surface. Alternatively, it has a ring groove surrounding an inner portion of the cover base which surrounds the through-opening. The desiccant-containing body may have an upper surface fit to this form such that the form fit is improved and the desiccant containing body is firmly attached by contacting the horizontal leg of the L-shaped profile of the cover base. Any other suitable sealing means may be provided if desired, in addition to the sealing means provided between the sealing through opening of the container base and the projection of the cover lid. As an example, an additional sealing means may be provided between a corresponding portion of the cover lid and the outer end of the above-mentioned groove in the cover base.

Other suitable sealing means are provided between the container wall and the cover base. It is already known to form suitable sealing rings with an increased press-fit and forming a line sealing between the container body and the cover base. Any other suitable sealing means may be used if desired, e.g. a small O-shaped ring made from an elastomer.

The foregoing will be more fully understood after a consideration of the following detailed description taken in conjunction with the accompanying drawings.

DETAILED DESCRIPTION

Figure 1:
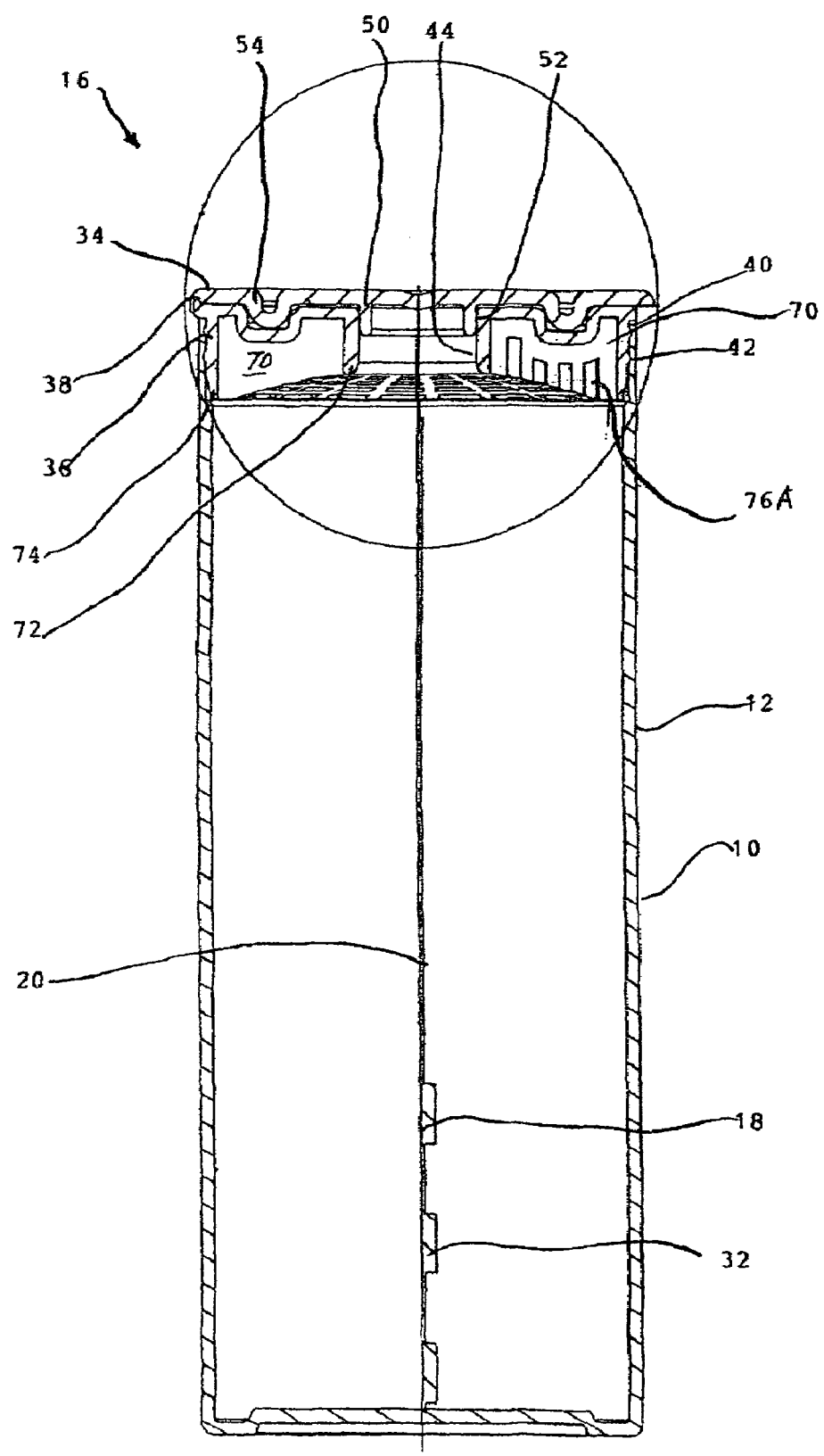
FIG. 1 is a cross-sectional view of a first embodiment of the container according to the invention.

FIG. 1 shows a preferred embodiment of the container according to the invention. The container 10 has a side wall 12, and a bottom, no number. In addition, the container is provided with a dispenser 20 which has moisture-sensitive goods 18 and 32 arranged on it. A cover 16 is formed of a cover lid 34 and of a cover base 36. A hinge 38 connects the cover lid 34 with the cover base 36.

The cover base 36 has two sealing rims 40 and 42 which extend at its circumference and act against a slightly thinner portion of the wall 12 of the container 10.

The cover base 36 at its center has a through-opening 44 as may be taken from FIG. 1. This through-opening 44 may be closed by a downwardly extending flange 50 of the cover lid 34 which has a snap-fit size suitable to firmly and tightly close the through-opening 44. The flange 50 at its outer circumference has sealing rims 52 which form a line seal against the through-opening 44.

As may be taken from FIG. 1, a further rim flange 54 is formed which stiffens the cover lid 34 and also forms a sort of an additional meander seal between the cover lid 34 and the cover base 36. A desiccant-containing body 70 is arranged close to the top of container 10. As may be taken form FIG. 1, the desiccant-containing body 70 is mounted at the lower end of cover base 36. The desiccant-containing body fully fills up a ring space formed between an inner flange 72 and an outer flange 74 of cover base 36.

The outer flange 74 protrudes more than inner flange 72 such that the lower surface of the desiccant containing body 70 is dome-shaped.

In this embodiment, the desiccant-containing body 70 has a plurality of holes 76A extending as blind holes from below. By this arrangement, the effective surface of the desiccant-containing body is greatly enhanced such that the desiccating effect improves.

While any suitable form of the desiccant-containing body may be selected, preferably the desiccant-containing body 70 has an equal thickness viewed from its surface. By this, all of its mass equally contributes to the desiccating effect.

In a further modified embodiment, (not illustrated), the lower surface of the desiccant-containing body 70 is covered by cardboard, web, or cloth, in order to achieve a suitable protection of the desiccant-containing body 70 against the goods. By selecting a suitable small size of the holes 76 the upper end of the dispenser 20 is prevented from entering the respective hole.

Figure 3:
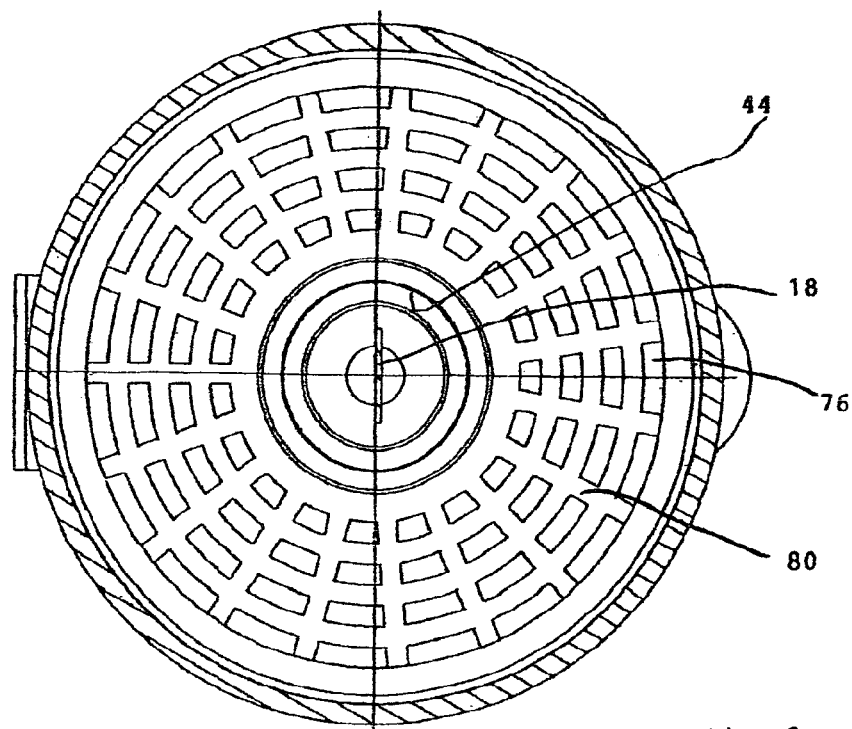
FIG. 3 is a bottom view of the cover base according to FIG. 1.
Figure 2:
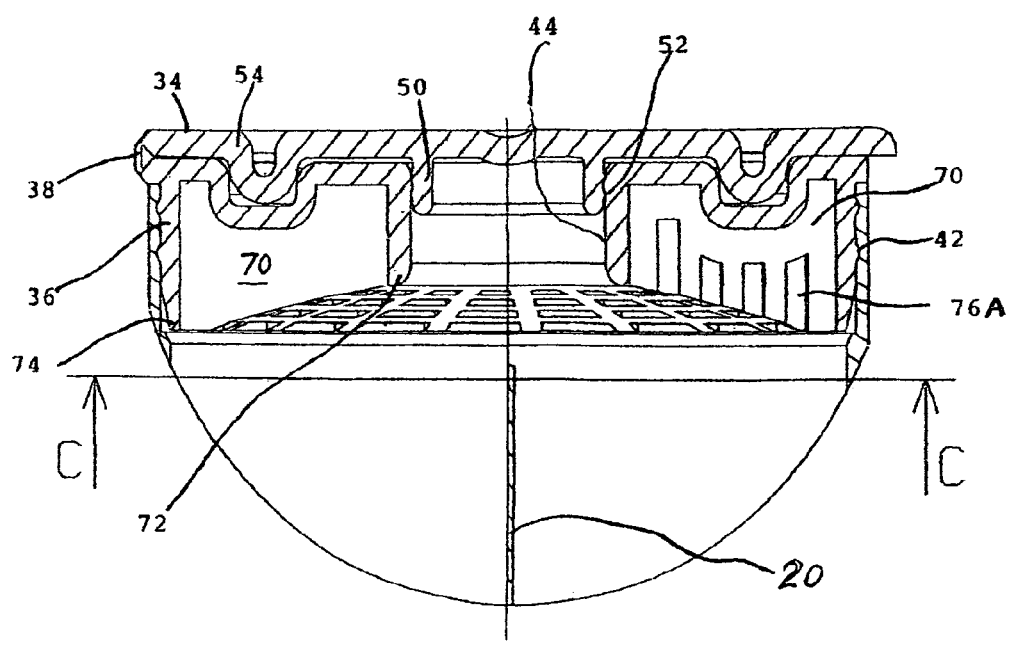
FIG. 2 is an enlarged view of a detail of the container according to FIG. 1.

FIG. 2 shows a part of the inventive container in a large scale while FIG. 3 shows a view of the cover base from below and along the line C-C in FIG. 2.

As may be taken from these figures, the dispenser 18 clearly fits through through-opening 44 while it does not fit even into the largest holes 76. By forming webs or ribs 80 between the holes 76, the dispenser is introduced into the through-opening 44 when turning the container upside-down. This effect is facilitated by the cone-shaped lower portion of body 70.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. Container for moisture-sensitive goods, the container including a container bottom, a container wall, and a cover, a portion of which cover may be opened and closed, the cover being provided with a desiccant-containing body, characterized in that
the cover (16) has a cover base (36) sealed to the wall of the container and a cover lid (34) which is pivotally secured to the cover base, the cover base (36) having a through-opening (44), the cover lid (34) being provided with sealing means for sealing the through-opening (44), and that the desiccant-containing body (70) is arranged within the cover base and at least partially surrounding the through-opening (44).

2. Container according to claim 1, characterized in that the desiccant-containing body (70) surrounds the through-opening (44).

3. Container according to claim 1, characterized in that the desiccant-containing body (70) is adjacent to the through opening (44).

4. Container according to claim 1, characterized in that the desiccant-containing body (70) has a ring-shape with an essentially flat upper surface and a concave lower surface.

5. Container according to claim 4, characterized in that the ring-shaped desiccant-containing body (70) has a sectional profile which is essentially a truncated right angle triangle, with an upper surface being close to the cover lid and a vertical leg of the triangle being essentially parallel to the outer wall of the container (10).

6. Container according to claim 5, characterized in that the hypothenuse of the triangle has an angle of 10° to 60°, against a horizontal portion of the cover base (36).

7. Container according to claim 1, characterized in that the cover base (36) and the cover lid (34) are formed integral to each other, with a hinge (38).

8. Container according to claim 1, characterized in that the cover lid (34) is provided with sealing means, the sealing means being formed with a projection protruding from a lower surface of the cover lid (34) and being sealed against the through opening in the cover base (36), in a closed position of the container (10).

9. Container according to claim 1, characterized in that additional sealing means are provided between an upper surface of the cover base (36) and a lower surface of the cover lid (34) forming a meander or labyrinth seal.

10. Container according to claim 1, wherein the moisture-sensitive goods (18) are fixed on or attached to strips, at their lower portions, and the strips have a length suitable to fit into the container (10) in an upright position.

11. Container according to claim 1, characterized in that a portion of the cover base (36) has an essentially L-shaped profile, with the lower leg of the L extending parallel to the container wall (12) and sealing against it and the upper leg of the L extending basically horizontally toward the through-opening (44).

12. Container according to claim 1, characterized in that the cover base (36) has an essentially L-shape profile with the desiccant-containing body (70) being received essentially between the legs of the L.

\* \* \* \* \*